United States Patent
Palti

[11] Patent Number: 5,846,188
[45] Date of Patent: Dec. 8, 1998

[54] SENSOR UTILIZING LIVING MUSCLE CELLS

[76] Inventor: Yoram Palti, 51 Ruth Street, Haifa, Israel

[21] Appl. No.: 783,946

[22] Filed: Jan. 17, 1997

[51] Int. Cl.$^6$ ...................................................... A61B 5/00
[52] U.S. Cl. ............................................................. 600/300
[58] Field of Search ................................... 600/300, 309, 600/473, 476; 604/31, 50, 66, 67; 250/461.2

[56] References Cited

U.S. PATENT DOCUMENTS

| | | | |
|---|---|---|---|
| 4,835,102 | 5/1989 | Bell et al. | 424/95 |
| 5,101,814 | 4/1992 | Palti . | |
| 5,190,041 | 3/1993 | Palti . | |
| 5,368,028 | 11/1994 | Palti . | |
| 5,474,552 | 12/1995 | Palti . | |
| 5,529,066 | 6/1996 | Palti . | |
| 5,608,519 | 3/1997 | Gourley et al. | 356/318 |

FOREIGN PATENT DOCUMENTS

| | | | |
|---|---|---|---|
| 33 45 196 A | 7/1985 | Germany . | |
| WO 96 00032 A | 1/1996 | WIPO . | |
| WO 96 04841 A | 2/1996 | WIPO . | |

*Primary Examiner*—John P. Lacyk
*Assistant Examiner*—Eric F. Winakur
*Attorney, Agent, or Firm*—Darby & Darby

[57] ABSTRACT

A system and method for monitoring a constituent or a condition in a medium. Living muscle cells are immersed in the medium. The muscle cells are sensitive to the constituent or condition and respond to exposure to the constituent or condition by physical movement. An optical measuring device measures the physical movement of the muscle cells and correlates the physical movement to a level of or a change in the level of the constituent or condition in the medium. The medium may be human tissue, with the muscle cells subcutaneously implanted therein. In one embodiment, a light source transmits a light beam toward the muscle cells. A reflector mounted to the muscle cells reflects the light beam, with the reflection angle varying with the physical movement of the muscle cells. A detector detects a change in the reflection angle and a processor correlates the change in the reflection angle to a change in the level of the constituent or condition in the medium. In an alternative embodiment, a photodetector detects the amount of light transmitted through and/or around the muscle cells. Electrodes may be attached to the muscle cells for stimulating the physical movement of the muscle cells. The muscle cells may be enclosed within a capsule. The capsule includes a portion that is transparent to light so as to enable movement of the cells to be monitored.

26 Claims, 5 Drawing Sheets

SENSOR UTILIZING LIVING MUSCLE CELLS

BACKGROUND OF THE INVENTION

1. Field of the Invention

The present invention relates generally to a sensor for monitoring a constituent or a condition in a medium, and more particularly to a sensor that utilizes living muscle cells that produce physical movement in response to the constituent or condition in the medium. An optical measuring device measures the movement of the muscle cells and correlates this movement to changes in the level of the constituent or condition.

2. Description of the Related Art

Various applications utilize sensors for the measurement and control of chemical concentration levels. For example, the concentration levels of certain chemicals, e.g., lead, fluoride, etc., in municipal water supplies are typically monitored so as to maintain the chemical levels within a predetermined range. The water supplies may also be monitored for the presence of toxic chemicals.

In environments in which hazardous materials may be present, e.g., industrial sites, the concentration of the hazardous materials in the ambient air and in other fluids at the site is also monitored and controlled. Similarly, in manufacturing processes, chemical levels in materials used during the processes are monitored and controlled. In many applications sensors are also used to detect the presence of physical parameters or conditions such as temperature, pressure, and pH.

The monitoring and control of medical conditions is another application in which sensors are used to measure and control constituent levels and physical conditions. Deviations from normal constituent levels in the blood and body tissues are associated with numerous diseases and physiological states. For instance, elevated blood and tissue potassium ion and urea levels are associated with kidney diseases; elevated blood glucose levels are associated with diabetes; and low thyroxin levels are associated with various thyroid gland malfunctions.

My prior U.S. Pat. Nos. 5,101,814 and 5,368,028, the contents of which are incorporated herein by reference, relate to a method of and apparatus for using subcutaneously implanted living cells as sensors, for monitoring blood glucose or other chemical levels. The living cells detect a constituent or condition in the body tissue and generate a chemical, electrical, or optical signal in response to the constituent or condition level in the tissue surrounding the cells. The signal is then detected and interpreted to provide a reading indicative of the constituent or condition level. The sensor reading can then be used to determine drug dosing, to control an implanted pump, or to provide any other desired treatment.

The living cells may be any type of cells that are sensitive to a specific constituent or condition, and that react to the constituent or condition by generating a chemical, electrical, or optical signal. For example, alpha and beta cells of the pancreas generate a predictable electrical signal in response to glucose levels in the medium surrounding the cells.

The living cells that are to be implanted may be contained in a capsule impermeable to large molecules, such as antibodies, and permeable to smaller molecules, such as nutrients. If the cells are of the type that generate an electrical signal in response to the constituent being detected, e.g., islets of Langerhans for detecting blood glucose levels, metallic electrodes in the capsule measure the electrical signal from the cells. The generation of electrical signals by such living cells, and the detection of such signals, is described in my aforesaid prior U.S. patents, and in my prior U.S. Pat. Nos. 5,190,041, and 5,529,066, the contents of each of which is incorporated herein by reference.

While U.S. Pat. Nos. 5,101,814 and 5,368,028 disclose the use of living cells as sensors, these cells are of the type that produce an electrical, chemical or optical signal in response to a constituent or condition to which the cells are sensitive. Other types of cells, e.g., muscle cells, undergo physical movement when exposed to a constituent or condition to which the cells are sensitive. Accordingly, a need exists for a sensor that uses the latter type of living cells to detect constituent and condition levels, and for an optical measurement system for detecting the movement of the living cells and for correlating the movement to a constituent or condition level based upon a predetermined response characteristic for the cells.

SUMMARY OF THE INVENTION

The present invention is a system for monitoring a constituent or a condition in a medium. The system utilizes living muscle cells that are immersed in the medium. The muscle cells are sensitive to the constituent or condition and respond to exposure to the constituent or condition by physical movement.

An optical measuring device measures the physical movement of the muscle cells and correlates the physical movement to a level of or a change in the level of the constituent or condition in the medium. In one embodiment, the medium is human body tissue and the muscle cells are subcutaneously implanted, either surgically or through a hypodermic needle. Alternatively, the medium may be any fluid in which it is desired to detect the constituent or condition to which the cells are sensitive.

An output device is connected to the optical measuring device. The output device may be, for example, i) an alarm for generating an alarm signal when the level of the constituent or condition in the medium is outside of a predetermined range, ii) a memory for storing the level of the constituent or condition over a period of time; or iii) a display for displaying the level of the constituent or condition.

In one embodiment, the optical measuring device includes a light source for transmitting a light beam toward the muscle cells, a reflector mounted to the muscle cells for reflecting the light beam, the reflection angle varying with the physical movement of the muscle cells, and a detector for detecting a change in the angle of reflection. A processor correlates the change in the angle of reflection to a change in the level of the constituent or condition in the medium.

In an alternative embodiment, the optical measuring device includes a light source for transmitting a light beam toward the muscle cells, and a photodetector for detecting the amount of light transmitted through and around the muscle cells. The muscle cells may be disposed between the light source and the photodetector, or the muscle cells may be disposed between the light source and a reflector, with the photodetector being positioned for receiving the light reflected by the reflector. A processor correlates a change in the fraction of light passing through and around the muscle cells to the level of the constituent or condition in the medium.

In another alternative embodiment, the optical measuring device includes a light source for transmitting a light beam toward the muscle cells, and a photodetector for detecting the amount of light passing through the muscle cells. The muscle cells may be disposed between the light source and the photodetector, or the muscle cells may disposed between the light source and a reflector, with the photodetector being positioned for receiving the light reflected by the reflector and for detecting the amount of light passing through the muscle cells. A processor correlates a change in the amount of light passing through the muscle cells to the level of the constituent or condition in the medium.

Electrodes may be attached to the muscle cells for stimulating the physical movement of the muscle cells. If the muscle cells are subcutaneously implanted, the optical measuring device is preferably at least partially disposed outside of the body. The optical measuring device may also include a subcutaneously implanted transmitter and a receiver located outside of the body, with the transmitter transmitting information related to the physical movement of the muscle cells to the receiver.

The muscle cells and the detector or reflector may be enclosed within a capsule. The capsule includes i) a membrane which is impermeable to large molecules and permeable to nutrients, and ii) a portion that is transparent to light.

A method of monitoring a constituent or a condition in a medium includes the steps of:

(a) immersing the living cells in the medium;

(b) optically measuring the physical movement of the muscle cells; and c) correlating the physical movement of the muscle cells to a level of or a change in the level of the constituent or condition in the medium.

Finally, a system for monitoring a constituent or a condition in a medium includes:

(a) living muscle cells of the type described above immersed in the medium;

(b) a capsule surrounding the living muscle cells, the capsule comprising a transparent portion; and (c) means for optically measuring the physical movement of the muscle cells through the transparent portion and for correlating the physical movement to a level of or a change in the level of the constituent or condition in the medium.

DETAILED DESCRIPTION OF THE INVENTION

The present invention is a sensor in which the element that performs the sensing is a mass of living muscle cells of the type that contract in a predetermined manner, or otherwise react with a predetermined physical movement, upon exposure to a constituent or when subject to a condition to which the muscle cells are sensitive. The muscle cells are then placed in an environment in which they are used to detect the chemical or condition to which they are sensitive.

Figure 1A:
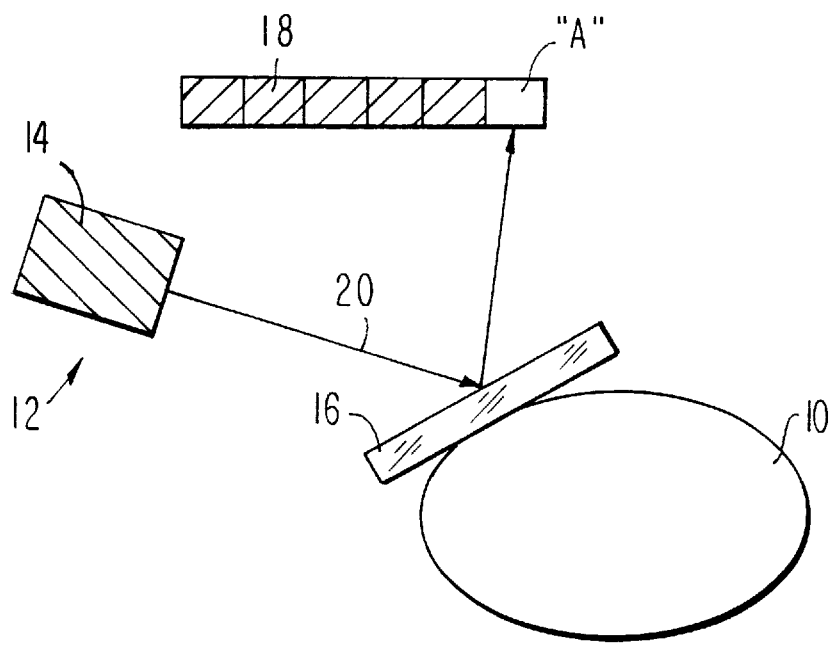
FIGS. 1A–1B show schematic views of the system of the present invention.

As shown in FIG. 1A, an optical detector 12 is placed in close proximity to living muscle cells 10 of the type described above in order to optically measure the movement response of the muscle cells. In a preferred embodiment, muscle cells 10 are subcutaneously implanted and are used to detect constituents or conditions in the human body. For subcutaneous applications, the cell mass 10 preferably measures less than 1 mm in diameter so that the cells may be injected through a hypodermic needle. For other applications, the cells may be placed in any environment in which it is desired to detect the constituent or condition to which the cells are sensitive.

Optical detector 12 is preferably located above the skin, in any desired housing, and optical measurements of the cell movement are taken transcutaneously. Optical detector 12 is preferably battery powered, although any desired power source may be utilized, and includes a light source 14, a reflector 16, and a detector 18. Light source 14 is a light bulb, an LED, a laser, or any other appropriate light source, and generates a light beam at any appropriate wavelength. In a preferred embodiment, the light beam is at infra-red or visible wavelengths, which may be transmitted transcutaneously without unacceptable losses. Reflector 16 is a mirror, metal surface, or any other material that reflects light. Reflector 16 is attached to muscle cells 10 by adhesive, or by any appropriate attachment technique. If desired, reflector 16 may be constructed of a non-reflective material coated with a material that reflects light.

Detector 18 receives the light reflected from reflector 16, and monitors the angle of the reflected light to detect changes in the relative contraction or movement of muscle cells 10. Detector 18 is preferably a linear array of light detecting elements such as photodetectors or charge coupled devices (CCD's). Each light detecting element generates an output signal indicative of the amount of light applied to that element, or a signal indicating when the amount of light applied to the element exceeds a threshold.

Figure 1B:
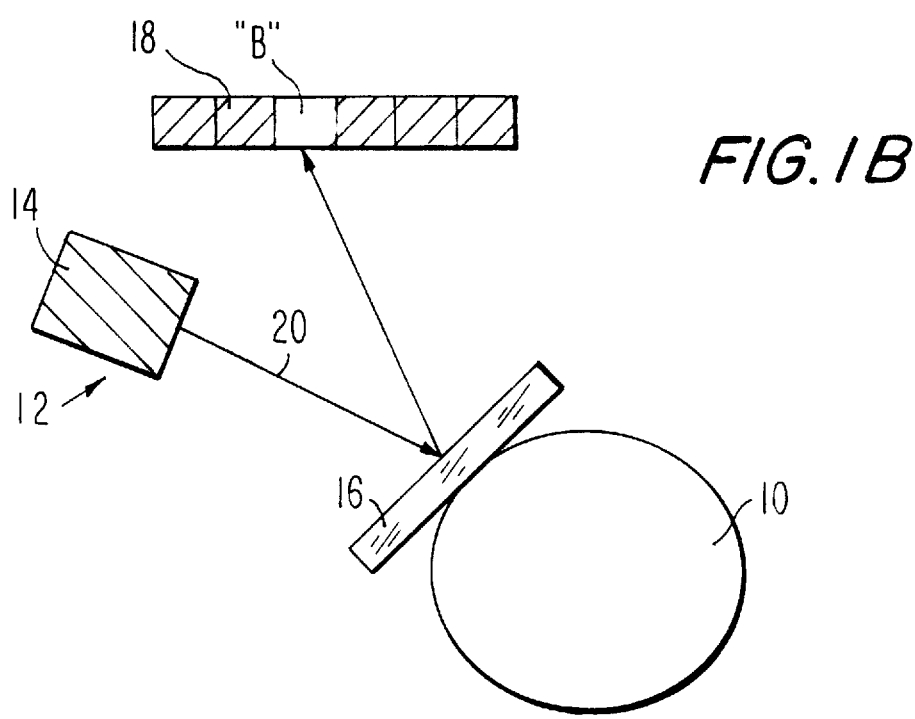

In operation, light source 14 directs a light beam 20 transcutaneously to reflector 16. Reflector 16 then reflects the light transcutaneously to detector 18. As shown in FIGS. 1A and 1B, the angle of reflection of the light beam 20 reaching the detector 18 changes in response to contraction of the muscle cells 10. FIG. 1A shows muscle cells 10 in a non-contracted state, with detector element "A" being illuminated. FIG. 1B shows muscle cells 10 in a contracted state, with detector element "B" being illuminated.

A processor (not shown) is connected to an output of detector 18. The processor monitors the elements of detector 18 that are illuminated and determines the change, or rate of change, in the angle of reflectance of light beam 20 based upon changes in the elements that are illuminated. The response characteristics of the living cells are predetermined so that the processor includes a look-up table to correlate movement of the cells to changes in the constituent or condition to which the cells are sensitive. Once the processor has determined angular movement of the reflector, it correlates[1/] to a change in the constituent or condition in the medium in which the muscle cells are located based upon the predetermined characteristics for the muscle cells.

[1/] The characteristics of such change (e.g., the magnitude or frequency of the change).

If desired, the processor may generate an output indicative of the constituent or condition level, an alarm signal may be generated, or corrective measures may be taken to adjust the constituent or condition level to within a desired range, etc.

As used herein, the "living muscle cells" may be any type of living matter, whether or not technically muscle cells, e.g., growth cones, that react with predetermined physical movement upon exposure to a constituent or when subject to a condition to which the living matter is sensitive. Such cells or portions thereof are normally subject to contraction, their contractile characteristics being changed upon exposure to the constituent or condition. In general, when the muscle cells are in a mass, the physical movement discussed herein refers to contraction or movement of the mass, rather than contraction or movement of the individual cells in the mass. The physical movement may be a variation in the rate of contraction of the muscle cells, a variation in the magnitude of the contraction, or both. Also, other contraction parameters, e.g., contraction duration, frequency, and the like, may be monitored, in addition to, or in lieu of, monitoring the intensity or rate of muscle cell contraction. For example, living cells 10 may be cardiac muscle cells. In this type of cell, the rate of contraction of the muscle cells changes in response to hormones such as adrenalin, to agents such as acetyl choline and various beta blockers, as well as to physical conditions such as mechanical stress, temperature, and other stimuli.

The muscle cells may alternatively be from the uterine and other muscles of the female reproductive system, which respond to hormones such as estrogens, progesterone, luteinizing hormone (LH), and other hormones, by changing their rate of contraction.

It will be understood that various types of muscle cells may be used in the system of the invention provided that the muscle cells are sensitive to the composition or condition being detected and that the mechanical aspects of the detection apparatus are modified in accordance with the type of response the cells exhibit to the composition or condition. It will also be appreciated that the system of the invention may be used in a variety of non-medical applications as well, such as monitoring water, air and other fluids for a variety of constituents or conditions.

Figure 2A:
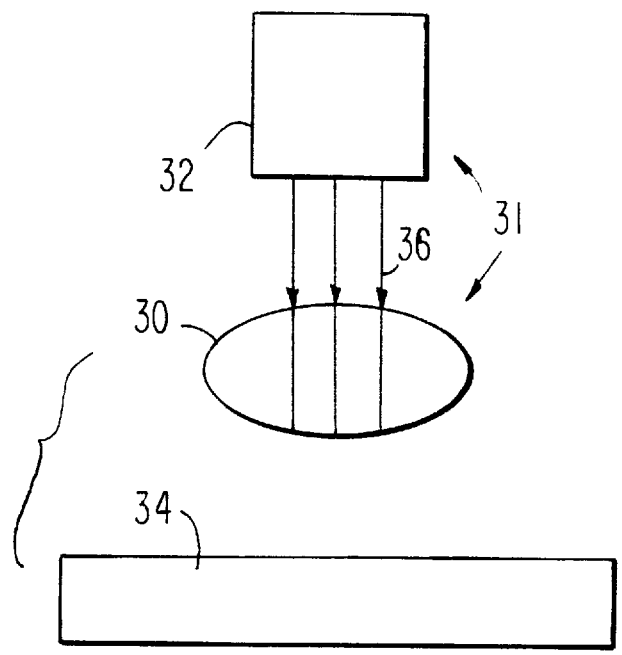
FIGS. 2A–2B show schematic views of an alternative embodiment of the system of the invention.
Figure 2B:
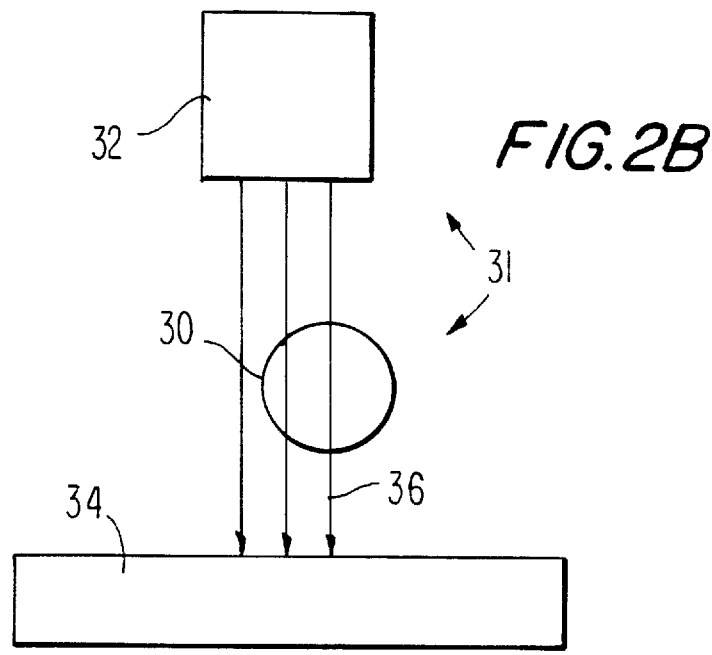

FIGS. 2A–2B show an alternative embodiment of the invention. Living muscle cells 30 of the type discussed above are implanted subcutaneously, either by injection or surgical implantation, or are placed in some other medium, in order to monitor a composition or condition to which cells 30 are sensitive in the body tissue or medium. An optical measurement apparatus 31, which is preferably located above the skin, includes a light source 32 of the type described above which directs a light beam 36 transcutaneously onto the muscle cells. While the muscle cells are preferably somewhat transparent to light, the size of the cell mass is chosen so that when the muscle cells 30 are in a non-contracted state (FIG. 2A), none of the light from light beam 36 is detectable by photodetector array 34, either because the light does not reach the array or because the array includes a threshold detector and the light reaching the array does not exceed the threshold. When muscle cells 30 contract due to a change in the chemical concentration or the presence of the condition, the light reaching photodetector 34 increases. This increase, or rate of increase, in the fraction of light beam 36 reaching photodetector 34 can be correlated to a change in the constituent or condition level by a processor (not shown) that is connected to the photodetector. It will be appreciated that the processor may be configured to determine the level of the chemical concentration or the presence of the condition based upon a change in the amount of light passing the muscle cells and reaching the photodetector. Accordingly, some light detection may occur at the photodetector with the muscle cells in an uncontracted state, if desired.

Figure 3A:
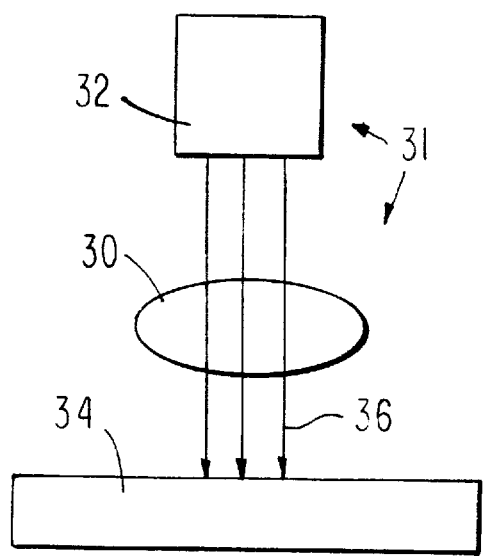
FIGS. 3A–3B show schematic views of another alternative embodiment of the system of the invention.
Figure 3B:
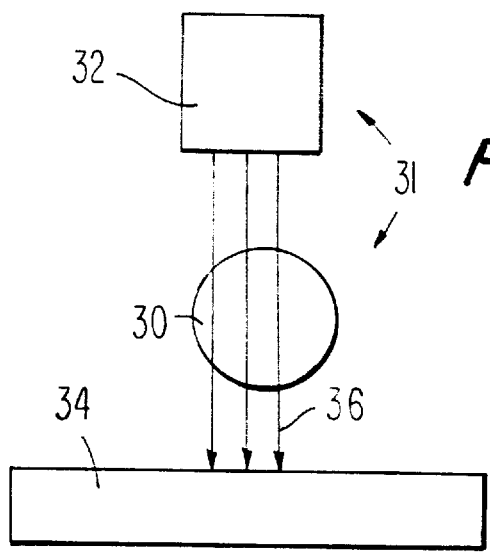

FIGS. 3A–3B show another alternative embodiment of the invention. In FIG. 3A, muscle cells 30 are shown in a non-contracted state. When a change in the constituent or condition level causes muscle cells 30 to contract, as shown in FIG. 3B, the amount of light absorbed by the muscle cells changes due to the mechanical response of the muscle cells. The stronger the contraction of the muscle cells 30, the longer the pathway of light through the muscle cells 30, thereby causing a larger attenuation of the light beam 36 and a lower intensity of light reaching the photodetector 34. If only the magnitude of the light passing the cell mass is used in the correlation process, photodetector 34 need not be an array of detectors, but may instead use a single photodetector that converts the amount of light received to an electrical signal.

Figure 4:
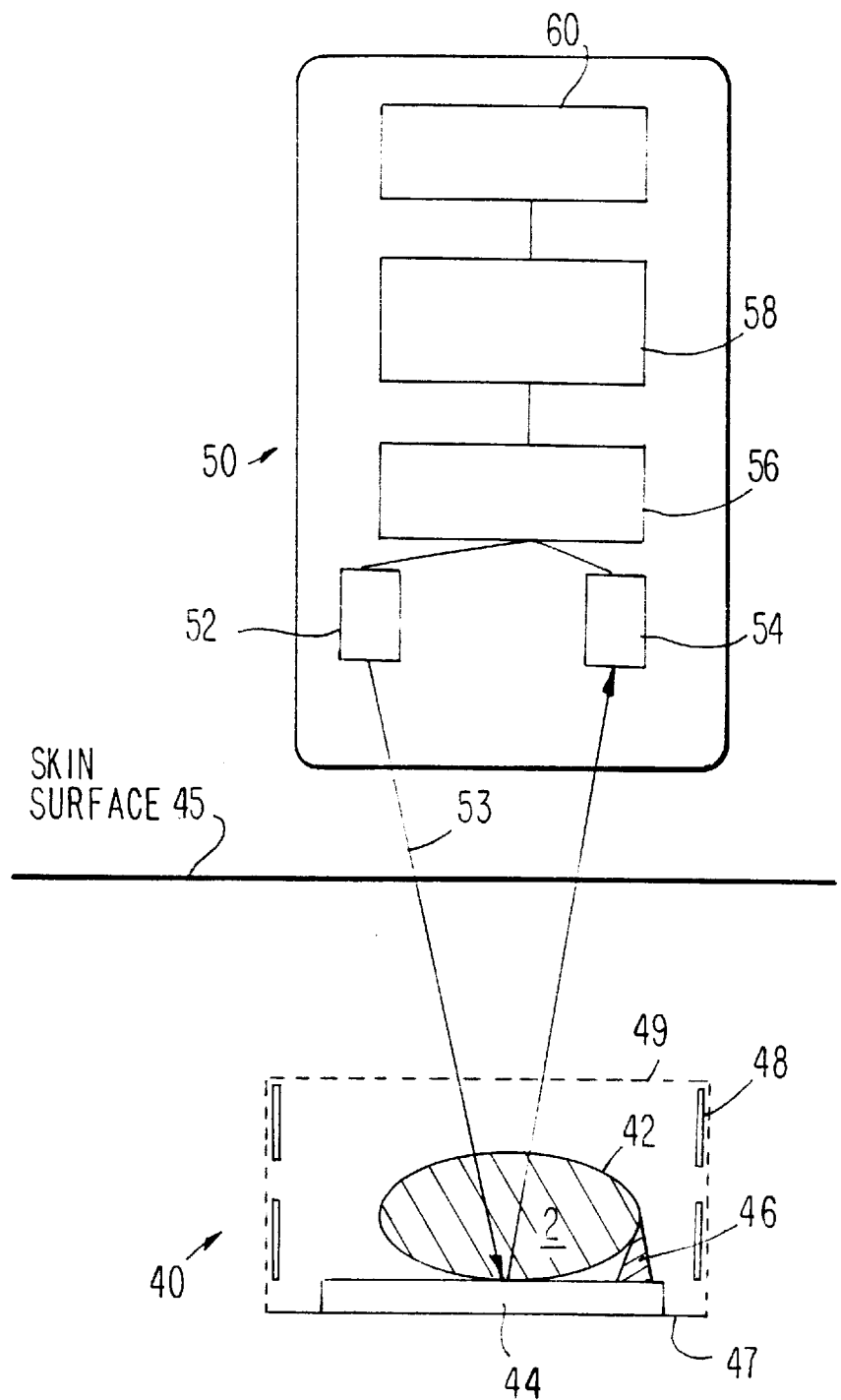
FIG. 4 shows a schematic view of another alternative embodiment of the invention in which the cells are enclosed in a capsule.

FIG. 4 illustrates an embodiment of the invention in which a capsule 40 contains muscle cells 42 and a reflector 44. Capsule 40 is preferably implanted under the skin surface 45 of a patient. Attaching means 46 may be provided for fastening reflector 44 to muscle cells 42. Attaching means 46 can be virtually any appropriate means for attaching muscle cells 42 to the reflector 44, including mechanical attaching means, chemical fastening means, adhesives and the like. In addition, muscle cells 42 can be fixed to the reflector at a single point, as shown in FIG. 4, or at multiple points (not shown).

Capsule 40 comprises outer walls 47 which extend completely around the living cells. As discussed in more detail below, a portion of the outer walls of the capsule includes a membrane 48 which is impermeable to large molecules and permeable to nutrients necessary for survival of the muscle cells. A portion 49 of the capsule is transparent to light.

An external optical measuring device 50 is positioned above the skin for measuring changes in the muscle cells. Measuring device 50 includes a light source 52 for directing a light beam 53 at reflector 44, and a detector 54 for measuring the change in quantity or intensity of the light reflected by reflector 44 due to movement of the muscle cells in response to a change in the constituent or condition level in proximity to the muscle cells. A processor 56 connected to detector 54 determines the movement of the muscles cells from the amount of light received at the detector, and correlates this to the change in the constituent or condition level. This information is transmitted to output means 58, which may be a display, an alarm, or any other appropriate output device, or the information may simply be recorded for later playback. Optional means for taking corrective measures 60, e.g., a pump, is connected to output means 58.

Measuring device 50 is preferably either hand held or attached to the skin near the site where capsule 40 has been implanted. For example, measuring device 50 can be strapped to the body like a wrist watch, applied in an adhesive patch, or may be attached by other fastening means such as adhesives and the like. In order to maintain the alignment of the measuring device with the capsule, a transcutaneous attachment, e.g., a very thin wire, may be made between the measuring device and the capsule. For non-medical applications, the alignment may be maintained by any appropriate physical structure.

In operation, light source 52 transmits a light beam 53 through muscle cells 42, and back to detector 54. A change in the chemical concentration or condition to which the cells are sensitive affects contraction of the muscle cells 42, which causes a detectable change in the intensity of the light beam 53 reflected from reflector 44 back to detector 54.

Detector 54 detects the change, or rate of change, in intensity of the light beam 53 and processor 56 correlates this change with the predetermined response characteristics for the muscle cells.

Figure 5:
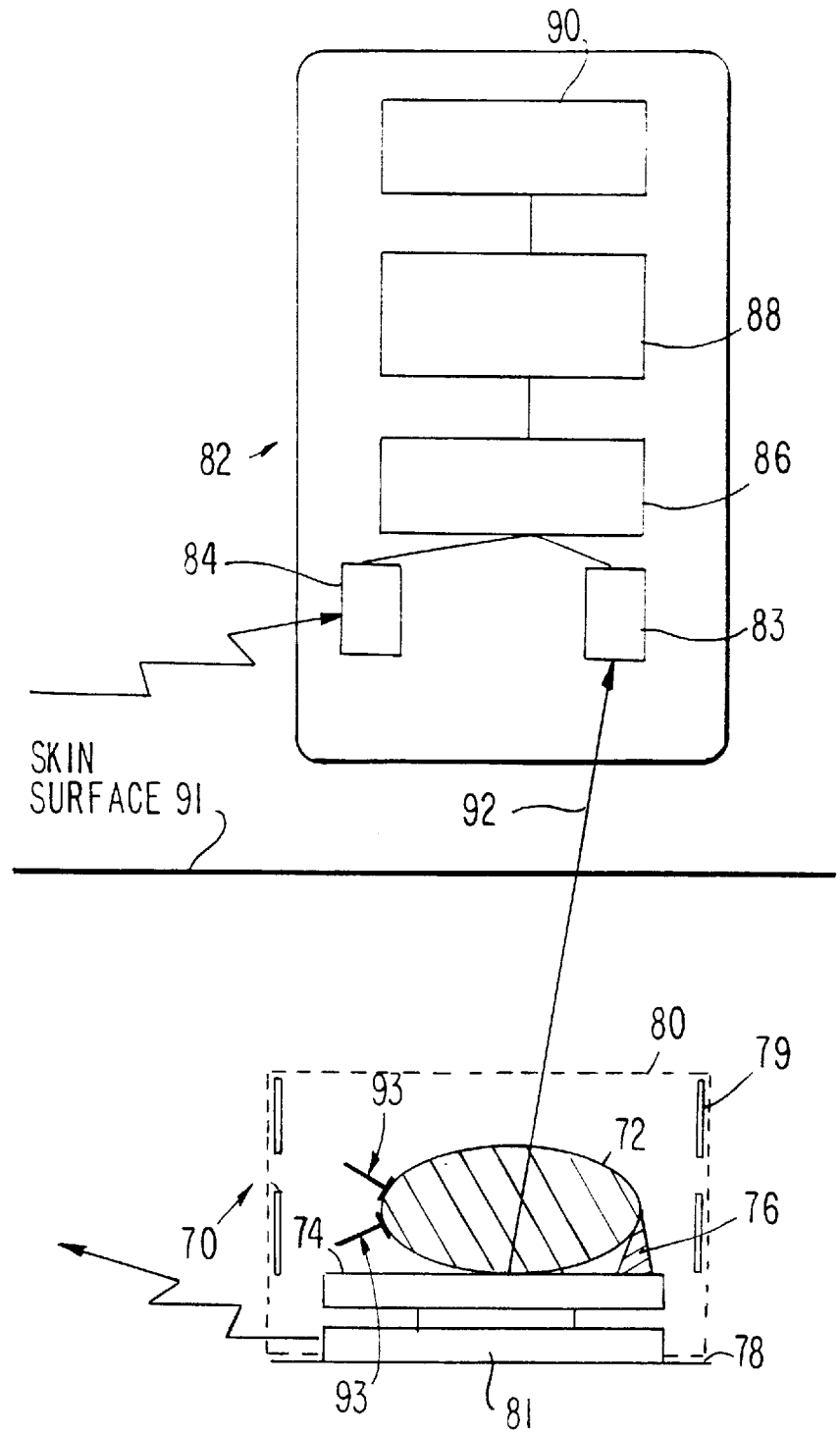
FIG. 5 shows a schematic view of another alternative embodiment of the present invention in which the cells are enclosed in a capsule.

FIG. 5 depicts still another embodiment of the invention. A subcutaneously implanted capsule 70 surrounds muscle cells 72 and a photodetector 74. Attaching means 76 fastens muscle cells 72 to photodetector 74. A portion of the outer walls 78 of the capsule comprises a membrane 79 which is impermeable to large molecules and permeable to the nutrients necessary for survival of muscle cells 72. Capsule 70 has a portion 80 which is transparent to light.

A transmitter 81 receives and amplifies the output of photodetector 74, and transmits the output to the skin surface. Measuring device 82, which is located above the skin surface, includes a light source 83, which generates a light beam 92, and a receiver 84. Transmitter 81 and receiver 84 are preferably compatible so that a signal generated by transmitter 81 is received by receiver 84. Transmitter 81 is preferably a conventional RF or microwave transmitter. Power may be supplied either directly to the transmitter by means of a battery or precharged capacitor (not shown) that is implanted with the capsule, by indirect means from above the skin such as by inductive or capacitive coupling, or by implanting a photocell that powers the transmitter using the light from light source 83. Transmitter 81 may be any type of communication device capable of transmitting a signal from below the skin surface to above the skin surface. A processor 86 correlates the mechanical movement of the muscle cells to a change in the chemical concentration or the presence of the condition to which the cells are sensitive. The processor transmits the correlated value to an output or storage device 88. Optional means for generating an alarm signal or taking corrective measures 90 is connected to the output means 88.

In operation, the capsule 70 is implanted under a patient's skin surface 91. Due to the size of the transmitter, it may be necessary for the implantation to be surgical. Measuring device 82 is held over the capsule, or attached to the patient's body near the site of the capsule. Light source 83 directs a light beam 92 through the muscle cells 72 to photodetector 74. Transmitter 81 amplifies and transmits the signal received by the photodetector 74, which is detected telemetrically through the skin surface 91 by receiver 84.

Many types of muscle cells spontaneously exhibit the physical movement described herein, e.g., contraction, with the changes in the movement, e.g., changes in the magnitude, rate, duration, frequency, etc., of the contraction, upon exposure to the constituent or condition, also being spontaneous. Certain other types of muscle cells may not spontaneously respond to the constituent or condition to which the cells are sensitive, but require an external stimulus to exhibit such a response. Accordingly, optional electrodes 93 are provided in contact with the muscle cells to periodically electrically stimulate the muscle cells 72. The electrodes are powered by the battery or other power source and are used to cause the muscle cells to respond to changes in the composition or condition level. In practice, the cells are stimulated while light is being directed on the cells and while measurements of the movement are being taken. In this way, the cells exhibit the desired response, e.g., contraction at a rate or magnitude related to the constituent or condition level, while movement measurements are being taken.

In an alternative embodiment (not shown), the present system is used in combination with a system for detecting the electric, chemical or optical characteristics of the cells, as discussed in U.S. Pat. No. 5,368,028. Using two types of signals generated by the cell mass provides for improved system accuracy.

In embodiments of the invention wherein the cells are contained in a capsule, the implantation is preferably in a location where the skin is thin and relatively transparent, such as the inner (plantar) aspect of the distal part of the forearm. Generally speaking, the capsule is of the type described in my prior patents, the contents of which have been incorporated herein by reference. The capsule is preferably 0.3–1.0 mm in size, although the capsule may be sized to meet the needs of the application. At least some part of the capsule wall includes a semipermeable membrane that allows nutrients and excretions to enter and exit the capsule while blocking the movement of large molecules such as proteins and antibodies having molecular weights of about 30,000–50,000. The inward diffusion of nutrients and the outward diffusion of excretions in the capsule should be sufficient to support long term muscle cell survival.

If used in medical applications, the capsule is preferably constructed of biocompatible materials such as PSF (polysulfone) and PVC/PAN (polyvinyl chloride/polyacrylonitrile) polymers.

It will be appreciated that although the present invention has been described in detail with respect to particular embodiments, it may be modified in ways that will be appreciated by those skilled in the art. For example, when a light beam is applied to the muscle cells, a shadow is produced. A detector could be utilized to detect movement of the shadow and to correlate this movement with changes in the constituent or condition to which the cells are sensitive. The movement of the shadow can be detecting using any appropriate edge detecting technique.

More generally, although the present invention has been described in detail with respect to certain embodiments and examples, variations and modifications exist that are within the scope of the present invention as defined in the following claims.

What is claimed is:

1. A system for monitoring a constituent or a condition in a medium, the system comprising:
   (a) living muscle cells which have been excised and isolated from an animal body prior to incorporation in the system, the contractile characteristics of the cells changing upon exposure to the constituent or condition in the medium with resulting physical movement of the cells; and
   (b) means in optical alignment with the muscle cells for optically measuring the physical movement of the cells and for correlating the physical movement to a level of or a change in the level of the constituent or condition in the medium.

2. The system of claim 1 wherein the medium is a human body and wherein the muscle cells are adapted to be subcutaneously implanted in the body.

3. The system of claim 2 wherein the means for optically measuring the physical movement of the muscle cells is at least partially disposed outside of the human body.

4. The system of claim 3 wherein the means for optically measuring the physical movement of the muscle cells comprises a subcutaneously implanted transmitter and a receiver located outside of the body, the transmitter transmitting information related to the physical movement of the muscle cells to the receiver.

5. The system of claim 1 further comprising an output device connected to the means for optically measuring the physical movement of the muscle cells, the output device being selected from the group consisting of i) an alarm for generating an alarm signal when the level of the constituent or condition in the medium is outside of a predetermined range; ii) a memory for storing the level of the constituent or condition over a period of time; and iii) a display for displaying the level of the constituent or condition.

6. The system of claim 1 wherein the means for optically measuring the physical movement of the muscle cells comprises;

a light source for transmitting a light beam toward the muscle cells;

a reflector mounted to the muscle cells for reflecting the light beam, the angle of the reflection varying with the physical movement of the muscle cells; and a detector for detecting a change in the angle of reflection.

7. The system of claim 6 further comprising:

a processor for correlating the change in the angle of reflection to a change in the level of the constituent or condition in the medium.

8. The system of claim 7 further comprising an artificial capsule which is not part of an animal body, wherein the muscle cells and the reflector are enclosed within the capsule.

9. The system of claim 8 wherein the capsule comprises i) a membrane which is impermeable to large molecules and permeable to nutrients, and ii) a portion that is transparent to light.

10. The system of claim 1 wherein the means for optically measuring the physical movement of the muscle cells comprises a light source for transmitting a light beam toward the muscle cells, and a photodetector for detecting the amount of light passing through or transmitted beyond the muscle cells.

11. The system of claim 10 wherein the muscle cells are disposed between the light source and the photodetector.

12. The system of claim 11 further comprising an artificial capsule which is not part of an animal body, wherein the muscle cells and the photodetector are enclosed within the capsule.

13. The system of claim 10 wherein the means for optically measuring the physical movement of the muscle cells further comprises a reflector, the muscle cells being disposed between the light source and the reflector, the photodetector being positioned for receiving the light reflected by the reflector.

14. The system of claim 13 further comprising an artificial capsule which is not part of an animal body, wherein the muscle cells and the reflector are enclosed within the capsule.

15. The system of claim 10 wherein the means for optically measuring the physical movement of the muscle cells further comprises a processor for correlating a change in the fraction of light passing beyond the muscle cells to the level of the constituent or condition in the medium.

16. The system of claim 1 wherein the means for optically measuring the physical movement of the muscle cells further comprises a light source for transmitting a light beam toward the muscle cells, and a photodetector for detecting the amount of light passing through the muscle cells.

17. The system of claim 1 further comprising electrodes attached to the muscle cells for stimulating the physical movement of the muscle cells.

18. A method of monitoring a constituent or a condition in a medium, the method comprising the steps of:

(a) providing living muscle cells which have been excised and isolated from an animal body prior to use in the method, the contractile characteristics of the cells changing upon exposure to the constituent or condition in the medium with resulting physical movement of the cells, and placing the living cells in the medium;

(b) optically measuring the physical movement of the muscle cells; and (c) correlating the physical movement of the muscle cells to a level of or a change in the level of the constituent or condition in the medium.

19. The method of claim 18 wherein the medium is a human body and further comprising the step of surgically or hypodermically subcutaneously implanting the muscle cells.

20. The method of claim 18 wherein the optical measuring step comprises the steps of i) attaching a reflector to the muscle cells, ii) transmitting a beam of light at the reflector, the light beam being reflected at an angle by the reflector, the angle being related to the physical movement of the muscle cells, and iii) detecting the change in the angle of reflection.

21. The method of claim 20 wherein the muscle cells and the reflector are enclosed within an artificial capsule which is not part of an animal body.

22. The method of claim 18 wherein the correlating step comprises comparing the physical movement of the muscle cells to a predetermined response characteristic for the muscle cells, the response characteristic relating physical movement of the muscle cells responsive to the constituent or condition to the level of or a change in the level of the constituent or condition.

23. The method of claim 18 wherein the optical measuring step comprises transmitting a light beam toward the muscle cells, and detecting the amount of light passing through or transmitted beyond the muscle cells.

24. The method of claim 18 wherein the correlating step comprises correlating a change in the amount of light passing through or transmitted beyond the muscle cells to the level of the constituent or condition in the medium.

25. The method of claim 18 further comprising the step of stimulating the muscle cells prior to the optical measuring step.

26. A system for monitoring a constituent or a condition in a medium, the system comprising:

(a) solid, living muscle cells which have been excised and isolated from an animal body prior to incorporation in the system, the contractile characteristics of the cells changing upon exposure to the constituent or condition in the medium with resulting physical movement;

(b) an artificial capsule surrounding the living muscle cells, the capsule not being part of an animal body and comprising a transparent portion; and (c) means for optically measuring the physical movement of the muscle cells through the transparent portion of the capsule and for correlating the physical movement to a level of or a change in the level of the constituent or condition in the medium.

* * * * *